(12) United States Patent
Podhajsky

(10) Patent No.: US 8,034,052 B2
(45) Date of Patent: *Oct. 11, 2011

(54) APPARATUS AND METHOD FOR ELECTRODE THERMOSURGERY

(75) Inventor: Ronald J. Podhajsky, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/917,053

(22) Filed: Nov. 1, 2010

(65) Prior Publication Data

US 2011/0046621 A1 Feb. 24, 2011

Related U.S. Application Data

(63) Continuation of application No. 11/418,880, filed on May 5, 2006, now Pat. No. 7,846,158.

(51) Int. Cl.
 *A61B 18/14* (2006.01)
(52) U.S. Cl. ............................................. 606/41; 606/49
(58) Field of Classification Search .............. 606/41–42, 606/45, 49
 See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |

(Continued)

FOREIGN PATENT DOCUMENTS

CA  2 104 423  2/1994

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Michael Peffley
*Assistant Examiner* — Samantha Good

(57) ABSTRACT

An instrument for tissue ablation includes an elongated tissue-penetrating electrode including a rigid tubular member having a closed distal end defining an interior cavity extending from the closed distal end to a proximal end of the rigid tubular member. The rigid tubular member defines an electrically conductive surface capable of receiving electrical energy from the source of electrical energy. The instrument includes one or more electrically conductive segments on the electrode and configured to receive electrosurgical energy from the rigid tubular member. An insulation layer is disposed upon the electrode and defines an exposed portion of the electrode at the distal end. The instrument also includes at least one sensor that detects a temperature during ablation and a semiconductive material coated on the rigid tubular member that forms one or more resistive layers that connects the rigid tubular member with a corresponding electrically conductive segment.

17 Claims, 6 Drawing Sheets

U.S. PATENT DOCUMENTS

| | | |
|---|---|---|
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. et al. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,257,635 A | 11/1993 | Langberg |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,417,686 A | 5/1995 | Peterson et al. |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwardds et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |

| | | | | | |
|---|---|---|---|---|---|
| 5,573,534 A | 11/1996 | Stone | 5,882,567 A | 3/1999 | Cavallaro et al. |
| 5,573,535 A | 11/1996 | Viklund | 5,891,141 A | 4/1999 | Rydell |
| 5,575,805 A | 11/1996 | Li | 5,891,142 A | 4/1999 | Eggers et al. |
| 5,578,052 A | 11/1996 | Koros et al. | 5,893,863 A | 4/1999 | Yoon |
| 5,582,611 A | 12/1996 | Tsukagoshi et al. | 5,893,875 A | 4/1999 | O'Connor et al. |
| 5,585,896 A | 12/1996 | Yamazaki et al. | 5,893,877 A | 4/1999 | Gampp, Jr. et al. |
| 5,590,570 A | 1/1997 | LeMaire, III et al. | 5,902,301 A | 5/1999 | Olig |
| 5,601,601 A | 2/1997 | Tal et al. | 5,906,630 A | 5/1999 | Anderhub et al. |
| 5,603,711 A | 2/1997 | Parins et al. | 5,908,420 A | 6/1999 | Parins et al. |
| 5,603,723 A | 2/1997 | Aranyi et al. | 5,908,432 A | 6/1999 | Pan |
| 5,611,798 A | 3/1997 | Eggers | 5,911,719 A | 6/1999 | Eggers |
| 5,620,453 A | 4/1997 | Nallakrishnan | 5,913,874 A | 6/1999 | Berns et al. |
| 5,624,452 A | 4/1997 | Yates | 5,921,984 A | 7/1999 | Sutcu et al. |
| 5,626,578 A | 5/1997 | Tihon | 5,925,043 A | 7/1999 | Kumar et al. |
| 5,626,609 A | 5/1997 | Zvenyatsky et al. | 5,935,126 A | 8/1999 | Riza |
| 5,630,833 A | 5/1997 | Katsaros et al. | 5,944,718 A | 8/1999 | Austin et al. |
| 5,637,110 A | 6/1997 | Pennybacker et al. | 5,951,549 A | 9/1999 | Richardson et al. |
| 5,638,003 A | 6/1997 | Hall | 5,954,720 A | 9/1999 | Wilson et al. |
| 5,643,294 A | 7/1997 | Tovey et al. | 5,957,923 A | 9/1999 | Hahnen et al. |
| 5,647,869 A | 7/1997 | Goble et al. | 5,960,544 A | 10/1999 | Beyers |
| 5,647,871 A | 7/1997 | Levine et al. | 5,961,514 A | 10/1999 | Long et al. |
| 5,649,959 A | 7/1997 | Hannam et al. | 5,964,758 A | 10/1999 | Dresden |
| 5,658,281 A | 8/1997 | Heard | 5,976,132 A | 11/1999 | Morris |
| 5,662,667 A | 9/1997 | Knodel | 5,984,939 A | 11/1999 | Yoon |
| 5,665,100 A | 9/1997 | Yoon | 5,989,277 A | 11/1999 | LeMaire, III et al. |
| 5,667,526 A | 9/1997 | Levin | 5,997,565 A | 12/1999 | Inoue |
| 5,674,220 A | 10/1997 | Fox et al. | 6,004,335 A | 12/1999 | Vaitekunas et al. |
| 5,681,282 A | 10/1997 | Eggers et al. | 6,010,516 A | 1/2000 | Hulka et al. |
| 5,688,270 A | 11/1997 | Yates et al. | 6,016,452 A | 1/2000 | Kasevich |
| 5,693,051 A | 12/1997 | Schulze et al. | 6,024,741 A | 2/2000 | Williamson et al. |
| 5,695,522 A | 12/1997 | LeMaire, III et al. | 6,024,744 A | 2/2000 | Kese et al. |
| 5,700,261 A | 12/1997 | Brinkerhoff | 6,030,384 A | 2/2000 | Nezhat |
| 5,702,390 A | 12/1997 | Austin et al. | 6,033,399 A | 3/2000 | Gines |
| 5,707,369 A | 1/1998 | Vaitekunas et al. | 6,039,733 A | 3/2000 | Buysse et al. |
| 5,709,680 A | 1/1998 | Yates et al. | 6,041,679 A | 3/2000 | Slater et al. |
| 5,716,366 A | 2/1998 | Yates | 6,050,996 A | 4/2000 | Schmaltz et al. |
| 5,720,744 A | 2/1998 | Eggleston et al. | 6,053,914 A | 4/2000 | Eggers et al. |
| 5,722,421 A | 3/1998 | Francese et al. | 6,053,933 A | 4/2000 | Balazs et al. |
| 5,725,536 A | 3/1998 | Oberlin et al. | D424,694 S | 5/2000 | Tetzlaff et al. |
| 5,727,428 A | 3/1998 | LeMaire, III et al. | D425,201 S | 5/2000 | Tetzlaff et al. |
| 5,735,848 A | 4/1998 | Yates et al. | 6,059,782 A | 5/2000 | Novak et al. |
| 5,743,906 A | 4/1998 | Parins et al. | 6,074,386 A | 6/2000 | Goble et al. |
| 5,755,717 A | 5/1998 | Yates et al. | RE36,795 E | 7/2000 | Rydell |
| 5,766,130 A | 6/1998 | Selmonosky | 6,083,223 A | 7/2000 | Baker |
| 5,766,166 A | 6/1998 | Hooven | 6,086,586 A | 7/2000 | Hooven |
| 5,766,170 A | 6/1998 | Eggers | 6,090,107 A | 7/2000 | Borgmeier et al. |
| 5,769,849 A | 6/1998 | Eggers | 6,096,037 A | 8/2000 | Mulier et al. |
| 5,772,655 A | 6/1998 | Bauer et al. | 6,099,550 A | 8/2000 | Yoon |
| 5,772,670 A | 6/1998 | Brosa | 6,102,909 A | 8/2000 | Chen et al. |
| 5,776,128 A | 7/1998 | Eggers | 6,110,171 A | 8/2000 | Rydell |
| 5,776,130 A | 7/1998 | Buysse et al. | 6,113,596 A | 9/2000 | Hooven et al. |
| 5,779,701 A | 7/1998 | McBrayer et al. | 6,113,598 A | 9/2000 | Baker |
| H1745 H | 8/1998 | Paraschac | 6,117,158 A | 9/2000 | Measamer et al. |
| 5,792,137 A | 8/1998 | Carr et al. | 6,123,701 A | 9/2000 | Nezhat |
| 5,792,177 A | 8/1998 | Kaseda | H1904 H | 10/2000 | Yates et al. |
| 5,797,927 A | 8/1998 | Yoon | 6,126,658 A | 10/2000 | Baker |
| 5,797,938 A | 8/1998 | Paraschac et al. | 6,152,923 A | 11/2000 | Ryan |
| 5,797,941 A | 8/1998 | Schulze et al. | 6,162,216 A | 12/2000 | Guziak et al. |
| 5,797,958 A | 8/1998 | Yoon | 6,162,220 A | 12/2000 | Nezhat |
| 5,800,449 A | 9/1998 | Wales | 6,174,309 B1 | 1/2001 | Wrublewski et al. |
| 5,807,393 A | 9/1998 | Williamson, IV et al. | 6,179,834 B1 | 1/2001 | Buysse et al. |
| 5,810,808 A | 9/1998 | Eggers | 6,179,837 B1 | 1/2001 | Hooven |
| 5,810,811 A | 9/1998 | Yates et al. | 6,183,467 B1 | 2/2001 | Shapeton et al. |
| 5,810,877 A | 9/1998 | Roth et al. | 6,187,003 B1 | 2/2001 | Buysse et al. |
| 5,814,043 A | 9/1998 | Shapeton | 6,190,386 B1 | 2/2001 | Rydell |
| 5,817,093 A | 10/1998 | Williamson, IV et al. | 6,193,718 B1 | 2/2001 | Kortenbach et al. |
| 5,820,630 A | 10/1998 | Lind | 6,206,876 B1 | 3/2001 | Levine et al. |
| 5,827,271 A | 10/1998 | Buysse et al. | 6,206,877 B1 | 3/2001 | Kese et al. |
| 5,827,279 A | 10/1998 | Hughett et al. | 6,217,602 B1 | 4/2001 | Redmon |
| 5,827,281 A | 10/1998 | Levin | 6,221,039 B1 | 4/2001 | Durgin et al. |
| 5,827,323 A | 10/1998 | Klieman et al. | 6,224,593 B1 | 5/2001 | Ryan et al. |
| 5,827,548 A | 10/1998 | Lavallee et al. | 6,228,080 B1 | 5/2001 | Gines |
| 5,833,690 A | 11/1998 | Yates et al. | 6,228,083 B1 | 5/2001 | Lands et al. |
| 5,843,075 A | 12/1998 | Taylor | 6,267,761 B1 | 7/2001 | Ryan |
| 5,843,080 A | 12/1998 | Fleenor et al. | 6,270,497 B1 | 8/2001 | Sekino et al. |
| 5,849,022 A | 12/1998 | Sakashita et al. | 6,270,508 B1 | 8/2001 | Klieman et al. |
| 5,853,412 A | 12/1998 | Mayenberger | 6,273,887 B1 | 8/2001 | Yamauchi et al. |
| 5,860,976 A | 1/1999 | Billings et al. | 6,277,117 B1 | 8/2001 | Tetzlaff et al. |
| 5,876,401 A | 3/1999 | Schulze et al. | 6,280,458 B1 | 8/2001 | Boche et al. |

| Patent No. | Date | Inventor |
|---|---|---|
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,413,255 B1 | 7/2002 | Stern |
| 6,419,675 B1 | 7/2002 | Gallo, Sr. |
| 6,421,567 B1 * | 7/2002 | Witte .................. 607/122 |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,506,189 B1 * | 1/2003 | Rittman et al. .................. 606/41 |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,575,969 B1 | 6/2003 | Rittman, III et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| 7,197,363 B2 | 3/2007 | Prakash et al. |
| D541,418 S | 4/2007 | Schechter et al. |
| 7,207,990 B2 | 4/2007 | Lands et al. |
| D541,938 S | 5/2007 | Kerr et al |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |

| | | | | | | |
|---|---|---|---|---|---|---|
| 7,329,257 B2 | 2/2008 | Kanehira et al. | | 2005/0149151 A1 | 7/2005 | Orszulak et al. |
| D564,662 S | 3/2008 | Moses et al. | | 2005/0187547 A1 | 8/2005 | Sugi |
| 7,342,754 B2 | 3/2008 | Fitzgerald et al. | | 2005/0197659 A1 | 9/2005 | Bahney |
| 7,344,268 B2 | 3/2008 | Jigamian | | 2005/0203504 A1 | 9/2005 | Wham et al. |
| 7,367,976 B2 | 5/2008 | Lawes et al. | | 2005/0240179 A1 | 10/2005 | Buysse et al. |
| D606,203 S | 12/2009 | Husheer et al. | | 2006/0052778 A1 | 3/2006 | Chapman et al. |
| D613,412 S | 4/2010 | DeCarlo | | 2006/0064085 A1 | 3/2006 | Schechter et al. |
| 7,846,158 B2 * | 12/2010 | Podhajsky .................. 606/41 | | 2006/0074417 A1 | 4/2006 | Cunningham et al. |
| 2002/0013583 A1 | 1/2002 | Camran et al. | | 2006/0079888 A1 | 4/2006 | Mulier et al. |
| 2002/0049442 A1 | 4/2002 | Roberts et al. | | 2006/0079890 A1 | 4/2006 | Guerra |
| 2002/0099372 A1 | 7/2002 | Schulze et al. | | 2006/0079891 A1 | 4/2006 | Arts et al. |
| 2002/0107517 A1 | 8/2002 | Witt et al. | | 2006/0116675 A1 | 6/2006 | McClurken et al. |
| 2002/0111624 A1 | 8/2002 | Witt et al. | | 2006/0129146 A1 | 6/2006 | Dycus et al. |
| 2002/0188294 A1 | 12/2002 | Couture et al. | | 2006/0161150 A1 | 7/2006 | Keppel |
| 2003/0014052 A1 | 1/2003 | Buysse et al. | | 2006/0167450 A1 | 7/2006 | Johnson et al. |
| 2003/0014053 A1 | 1/2003 | Nguyen et al. | | 2006/0167452 A1 | 7/2006 | Moses et al. |
| 2003/0018331 A1 | 1/2003 | Dycus et al. | | 2006/0173452 A1 | 8/2006 | Buysse et al. |
| 2003/0018332 A1 | 1/2003 | Schmaltz et al. | | 2006/0189980 A1 | 8/2006 | Johnson et al. |
| 2003/0032956 A1 | 2/2003 | Lands et al. | | 2006/0189981 A1 | 8/2006 | Dycus et al. |
| 2003/0069571 A1 | 4/2003 | Treat et al. | | 2006/0190035 A1 | 8/2006 | Hushka et al. |
| 2003/0078578 A1 | 4/2003 | Truckai et al. | | 2006/0217709 A1 | 9/2006 | Couture et al. |
| 2003/0109875 A1 | 6/2003 | Tetzlaff et al. | | 2006/0224158 A1 | 10/2006 | Odom et al. |
| 2003/0114851 A1 | 6/2003 | Truckai et al. | | 2006/0259036 A1 | 11/2006 | Tetzlaf et al. |
| 2003/0139741 A1 | 7/2003 | Goble et al. | | 2006/0264922 A1 | 11/2006 | Sartor et al. |
| 2003/0139742 A1 | 7/2003 | Wampler et al. | | 2006/0264931 A1 | 11/2006 | Chapman et al. |
| 2003/0158549 A1 | 8/2003 | Swanson | | 2006/0271038 A1 | 11/2006 | Johnson et al. |
| 2003/0181910 A1 | 9/2003 | Dycus et al. | | 2006/0287641 A1 | 12/2006 | Perlin |
| 2003/0195501 A1 | 10/2003 | Sherman et al. | | 2007/0016182 A1 | 1/2007 | Lipson et al. |
| 2003/0199869 A1 | 10/2003 | Johnson et al. | | 2007/0016187 A1 | 1/2007 | Weinberg et al. |
| 2003/0216732 A1 | 11/2003 | Truckai et al. | | 2007/0043352 A1 | 2/2007 | Garrison et al. |
| 2003/0220637 A1 | 11/2003 | Truckai et al. | | 2007/0043353 A1 | 2/2007 | Dycus et al. |
| 2003/0229344 A1 | 12/2003 | Dycus et al. | | 2007/0055231 A1 | 3/2007 | Dycus et al. |
| 2004/0030330 A1 | 2/2004 | Brassell et al. | | 2007/0060919 A1 | 3/2007 | Isaacson et al. |
| 2004/0030332 A1 | 2/2004 | Knowlton et al. | | 2007/0062017 A1 | 3/2007 | Dycus et al. |
| 2004/0049185 A1 | 3/2004 | Latterell et al. | | 2007/0074807 A1 | 4/2007 | Guerra |
| 2004/0064151 A1 | 4/2004 | Mollenauer | | 2007/0078456 A1 | 4/2007 | Dumbauld et al. |
| 2004/0078035 A1 | 4/2004 | Kanehira et al. | | 2007/0078458 A1 | 4/2007 | Dumbauld et al. |
| 2004/0082952 A1 | 4/2004 | Dycus et al. | | 2007/0078459 A1 | 4/2007 | Johnson et al. |
| 2004/0087943 A1 | 5/2004 | Dycus et al. | | 2007/0088356 A1 | 4/2007 | Moses et al. |
| 2004/0115296 A1 | 6/2004 | Duffin | | 2007/0106295 A1 | 5/2007 | Garrison et al. |
| 2004/0116924 A1 | 6/2004 | Dycus et al. | | 2007/0106297 A1 | 5/2007 | Dumbauld et al. |
| 2004/0116979 A1 | 6/2004 | Truckai et al. | | 2007/0118111 A1 | 5/2007 | Weinberg |
| 2004/0122423 A1 | 6/2004 | Dycus et al. | | 2007/0118115 A1 | 5/2007 | Artale et al. |
| 2004/0143236 A1 | 7/2004 | Santini et al. | | 2007/0142833 A1 | 6/2007 | Dycus et al. |
| 2004/0143263 A1 | 7/2004 | Schechter et al. | | 2007/0142834 A1 | 6/2007 | Dumbauld |
| 2004/0147925 A1 | 7/2004 | Buysse et al. | | 2007/0156139 A1 | 7/2007 | Schechter et al. |
| 2004/0162557 A1 | 8/2004 | Tetzlaff et al. | | 2007/0156140 A1 | 7/2007 | Baily |
| 2004/0176762 A1 | 9/2004 | Lawes et al. | | 2007/0173811 A1 | 7/2007 | Couture et al. |
| 2004/0193153 A1 | 9/2004 | Sarter et al. | | 2007/0173814 A1 | 7/2007 | Hixson et al. |
| 2004/0225288 A1 | 11/2004 | Buysse et al. | | 2007/0179497 A1 | 8/2007 | Eggers et al. |
| 2004/0230189 A1 | 11/2004 | Keppel | | 2007/0179499 A1 | 8/2007 | Garrison |
| 2004/0236325 A1 | 11/2004 | Tetzlaff et al. | | 2007/0198006 A1 | 8/2007 | Prakash et al. |
| 2004/0236326 A1 | 11/2004 | Schulze et al. | | 2007/0203485 A1 | 8/2007 | Keppel |
| 2004/0243125 A1 | 12/2004 | Dycus et al. | | 2007/0213706 A1 | 9/2007 | Dumbauld et al. |
| 2004/0249371 A1 | 12/2004 | Dycus et al. | | 2007/0213707 A1 | 9/2007 | Dumbauld et al. |
| 2004/0249374 A1 | 12/2004 | Tetzlaff et al. | | 2007/0213708 A1 | 9/2007 | Dumbauld et al. |
| 2004/0249425 A1 | 12/2004 | Roy et al. | | 2007/0213712 A1 | 9/2007 | Buysse et al. |
| 2004/0250419 A1 | 12/2004 | Sremcich et al. | | 2007/0255279 A1 | 11/2007 | Buysse et al. |
| 2004/0254573 A1 | 12/2004 | Dycus et al. | | 2007/0260235 A1 | 11/2007 | Podhajsky |
| 2004/0260281 A1 | 12/2004 | Baxter, III et al. | | 2007/0260237 A1 | 11/2007 | Sutton et al. |
| 2005/0004564 A1 | 1/2005 | Wham et al. | | 2007/0260238 A1 | 11/2007 | Guerra |
| 2005/0004568 A1 | 1/2005 | Lawes et al. | | 2007/0260241 A1 | 11/2007 | Dalla Betta et al. |
| 2005/0004570 A1 | 1/2005 | Chapman et al. | | 2007/0260242 A1 | 11/2007 | Dycus et al. |
| 2005/0021025 A1 | 1/2005 | Buysse et al. | | 2007/0265616 A1 | 11/2007 | Couture et al. |
| 2005/0021026 A1 | 1/2005 | Baily | | 2008/0004616 A1 | 1/2008 | Patrick |
| 2005/0021027 A1 | 1/2005 | Shields et al. | | 2008/0009860 A1 | 1/2008 | Odom |
| 2005/0033278 A1 | 2/2005 | McClurken et al. | | 2008/0015575 A1 | 1/2008 | Odom et al. |
| 2005/0096645 A1 | 5/2005 | Wellman et al. | | 2008/0021450 A1 | 1/2008 | Couture |
| 2005/0101951 A1 | 5/2005 | Wham et al. | | 2008/0033428 A1 | 2/2008 | Artale et al. |
| 2005/0101952 A1 | 5/2005 | Lands et al. | | 2008/0039835 A1 | 2/2008 | Johnson et al. |
| 2005/0107784 A1 | 5/2005 | Moses et al. | | 2008/0045947 A1 | 2/2008 | Johnson et al. |
| 2005/0107785 A1 | 5/2005 | Dycus et al. | | 2008/0058802 A1 | 3/2008 | Couture et al. |
| 2005/0113818 A1 | 5/2005 | Sartor et al. | | 2008/0082100 A1 | 4/2008 | Orton et al. |
| 2005/0113819 A1 | 5/2005 | Wham et al. | | | | |
| 2005/0113826 A1 | 5/2005 | Johnson et al. | | | FOREIGN PATENT DOCUMENTS | |
| 2005/0113827 A1 | 5/2005 | Dumbauld et al. | | CA | 2 520 413 | 3/2007 |
| 2005/0113828 A1 | 5/2005 | Shields et al. | | CN | 1103807 | 6/1995 |
| 2005/0119655 A1 | 6/2005 | Moses et al. | | DE | 390937 | 3/1924 |
| 2005/0149017 A1 | 7/2005 | Dycus | | DE | 1099658 | 2/1961 |

| | | | | | | |
|---|---|---|---|---|---|---|
| DE | 1139927 | 11/1962 | | EP | 0923907 | 6/1999 |
| DE | 1149832 | 6/1963 | | EP | 0950378 | 10/1999 |
| DE | 1439302 | 1/1969 | | EP | 0986990 | 3/2000 |
| DE | 2439587 | 2/1975 | | EP | 1034747 | 9/2000 |
| DE | 2455174 | 5/1975 | | EP | 1034748 | 9/2000 |
| DE | 2407559 | 8/1975 | | EP | 1025807 | 10/2000 |
| DE | 2415263 | 10/1975 | | EP | 1034746 | 10/2000 |
| DE | 2429021 | 1/1976 | | EP | 1050278 | 11/2000 |
| DE | 2460481 | 6/1976 | | EP | 1053719 | 11/2000 |
| DE | 2602517 | 7/1976 | | EP | 1053720 | 11/2000 |
| DE | 2504280 | 8/1976 | | EP | 1055399 | 11/2000 |
| DE | 2514501 | 10/1976 | | EP | 1055400 | 11/2000 |
| DE | 2627679 | 1/1977 | | EP | 1080694 | 3/2001 |
| DE | 2540968 | 3/1977 | | EP | 1082944 | 3/2001 |
| DE | 2820908 | 11/1978 | | EP | 1 159 926 | 5/2001 |
| DE | 2803275 | 8/1979 | | EP | 1177771 | 2/2002 |
| DE | 2823291 | 11/1979 | | EP | 1278007 | 1/2003 |
| DE | 2946728 | 5/1981 | | EP | 1301135 | 4/2003 |
| DE | 3143421 | 5/1982 | | EP | 1330991 | 7/2003 |
| DE | 3045996 | 7/1982 | | EP | 1486177 | 6/2004 |
| DE | 3120102 | 12/1982 | | EP | 1472984 | 11/2004 |
| DE | 3423356 | 1/1986 | | EP | 0774232 | 1/2005 |
| DE | 3510586 | 10/1986 | | EP | 1527747 | 5/2005 |
| DE | 3612646 | 4/1987 | | EP | 1530952 | 5/2005 |
| DE | 3604823 | 8/1987 | | EP | 1532932 | 5/2005 |
| DE | 8712328 | 3/1988 | | EP | 1535581 | 6/2005 |
| DE | 3711511 | 6/1988 | | EP | 1609430 | 12/2005 |
| DE | 3904558 | 8/1990 | | EP | 1201192 | 2/2006 |
| DE | 3942998 | 7/1991 | | EP | 1632192 | 3/2006 |
| DE | 4238263 | 5/1993 | | EP | 1642543 | 4/2006 |
| DE | 4303882 | 8/1994 | | EP | 1645238 | 4/2006 |
| DE | 4339049 | 5/1995 | | EP | 1645240 | 4/2006 |
| DE | 4403252 | 8/1995 | | EP | 1649821 | 4/2006 |
| DE | 19515914 | 7/1996 | | EP | 1707143 | 10/2006 |
| DE | 19506363 | 8/1996 | | EP | 1545360 | 3/2007 |
| DE | 29616210 | 1/1997 | | EP | 1767163 | 3/2007 |
| DE | 19608716 | 4/1997 | | EP | 1769765 | 4/2007 |
| DE | 19751106 | 5/1998 | | EP | 1769766 | 4/2007 |
| DE | 19717411 | 11/1998 | | EP | 1785097 | 5/2007 |
| DE | 19751108 | 5/1999 | | EP | 1785098 | 5/2007 |
| DE | 19801173 | 7/1999 | | EP | 1785101 | 5/2007 |
| DE | 19848540 | 5/2000 | | EP | 1810625 | 7/2007 |
| DE | 10045375 | 4/2002 | | EP | 1810628 | 7/2007 |
| DE | 10224154 | 12/2003 | | EP | 1842500 | 10/2007 |
| DE | 10310765 | 9/2004 | | EP | 1878400 | 1/2008 |
| DE | 10328514 | 3/2005 | | EP | 1929970 | 6/2008 |
| DE | 10 2004 026 179 | 12/2005 | | EP | 1990019 | 11/2008 |
| DE | 102004022206 | 12/2005 | | EP | 1683496 | 12/2008 |
| DE | 202005015147 | 3/2006 | | EP | 1997438 | 12/2008 |
| DE | 20 2007 009 165 | 10/2007 | | EP | 1997439 | 12/2008 |
| DE | 20 2007 009 317 | 10/2007 | | EP | 1527744 | 2/2009 |
| DE | 19738457 | 1/2009 | | EP | 2206474 | 7/2010 |
| EP | 0 246 350 | 11/1987 | | FR | 179 607 | 11/1906 |
| EP | 0364216 | 4/1990 | | FR | 1 275 415 | 10/1961 |
| EP | 0467501 | 1/1992 | | FR | 1 347 865 | 11/1963 |
| EP | 0509670 | 10/1992 | | FR | 2 235 669 | 1/1975 |
| EP | 0518230 | 12/1992 | | FR | 2 276 027 | 1/1976 |
| EP | 0 521 264 | 1/1993 | | FR | 2 313 708 | 12/1976 |
| EP | 0541930 | 5/1993 | | FR | 2 502 935 | 10/1982 |
| EP | 0 556 705 | 8/1993 | | FR | 2 517 953 | 6/1983 |
| EP | 0306123 | 8/1993 | | FR | 2 573 301 | 5/1986 |
| EP | 0 558 429 | 9/1993 | | FR | 2 862 813 | 5/2005 |
| EP | 0572131 | 12/1993 | | FR | 2 864 439 | 7/2005 |
| EP | 0584787 | 3/1994 | | GB | 623316 | 5/1949 |
| EP | 0589453 | 3/1994 | | GB | 1490585 | 11/1977 |
| EP | 0589555 | 3/1994 | | GB | 2214430 A | 6/1989 |
| EP | 0623316 | 11/1994 | | GB | 2213416 A | 8/1989 |
| EP | 0624348 | 11/1994 | | JP | 61-501068 | 9/1984 |
| EP | 0650701 | 5/1995 | | JP | 6-502328 | 3/1992 |
| EP | 0694290 | 3/1996 | | JP | 5-5106 | 1/1993 |
| EP | 0717966 | 6/1996 | | JP | 05-40112 | 2/1993 |
| EP | 0754437 | 3/1997 | | JP | 06343644 | 12/1994 |
| EP | 0517243 | 9/1997 | | JP | 07265328 | 10/1995 |
| EP | 0 836 868 | 4/1998 | | JP | 08056955 | 3/1996 |
| EP | 0853922 | 7/1998 | | JP | 08252263 | 10/1996 |
| EP | 0875209 | 11/1998 | | JP | 09000492 | 1/1997 |
| EP | 0878169 | 11/1998 | | JP | 09010223 | 1/1997 |
| EP | 0 882 955 | 12/1998 | | JP | 10-24051 | 1/1998 |
| EP | 0887046 | 1/1999 | | JP | 11-070124 | 5/1998 |

| | | |
|---|---|---|
| JP | 2000-102545 | 9/1998 |
| JP | 11-169381 | 6/1999 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 89/00757 | 1/1989 |
| WO | WO 92/04873 | 4/1992 |
| WO | WO 92/06642 | 4/1992 |
| WO | WO 93/19681 | 10/1993 |
| WO | WO 93/21845 | 11/1993 |
| WO | WO 94/00059 | 1/1994 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 95/20360 | 8/1995 |
| WO | WO 96/05776 | 2/1996 |
| WO | WO 96/11635 | 4/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/18768 | 5/1997 |
| WO | WO 97/24073 | 7/1997 |
| WO | WO 97/24993 | 7/1997 |
| WO | WO 98/14124 | 4/1998 |
| WO | WO 98/27880 | 7/1998 |
| WO | WO 98/31290 | 7/1998 |
| WO | WO 98/43264 | 10/1998 |
| WO | WO 99/03407 | 1/1999 |
| WO | WO 99/03408 | 1/1999 |
| WO | WO 99/03409 | 1/1999 |
| WO | WO 99/03414 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/33753 | 6/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/01847 | 1/2001 |
| WO | WO 01/15614 | 3/2001 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/028585 | 4/2004 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/048809 | 6/2005 |
| WO | WO 2005/050151 | 6/2005 |
| WO | WO 2005/110264 | 11/2005 |
| WO | WO 2008/008457 | 1/2008 |
| WO | WO 2008/040483 | 4/2008 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |
| WO | WO 2009/039179 | 3/2009 |
| WO | WO 2009/039510 | 3/2009 |
| WO | WO2010/035831 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.

Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/Wire Localizer, Namic® Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Durney et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 94In Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Crawford et al., "Use of the LigaSure™ Vessel Sealing System in Urologic Cancer Surgery" Grand Rounds in Urology 1999, vol. 1, Issue 4, pp. 10-17.

Crouch et al. "A Velocity-Dependent Model for Needle Insertion in Soft Tissue" MICCAI 2005; LNCS 3750 pp. 624-632, Dated: 2005.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com./lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part 1", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite-Element Codes to Model Electrical Heating and Non-LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

Levy et al. "Use of a New Energy-based Vessel Ligation Device During Vaginal Hysterectomy" Int'l Federation of Gynecology and Obstetrics (FIGO) World Congress 1999.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al. "Vessel Sealing for Hemostasis During Gynecologic Surgery" Sales/Product Literature 1999.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817·825.
Tinkcler L.F., "Combined Diathermy and Suction Forceps" , Feb. 6, 1967 (Feb. 6, 1965), British Medical Journal, vol. 1, nr. 5431 p. 361, ISSN: 0007-1447.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
Int'l Search Report EP 98957771 dated Aug. 9, 2001.
Int'l Search Report EP 98957773 dated Aug. 1, 2001.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
Int'l Search Report EP 04709033.7 dated Dec. 8, 2010.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
Int'l Search Report EP 05002671.5 dated Dec. 22, 2008.
Int'l Search Report EP 05002674.9 dated Jan. 16, 2009.
European Search Report EP 05002769.7 dated Jun. 19, 2006.
European Search Report EP 05013463.4 dated Oct. 7, 2005.
Int'l Search Report EP 05013894 dated Feb. 3, 2006.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
Int'l Search Report EP 05019429.9 dated May 6, 2008.
European Search Report EP 05019882 dated Feb. 16, 2006.
Int'l Search Report EP 05020532 dated Jan. 10, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
Int'l Search Report—extended—EP 05021937.7 dated Mar. 15, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.

Int'l Search Report EP 06006716.2 dated Aug. 4, 2006.
European Search Report EP 06006717.0 dated Aug. 11, 2006.
European Search Report EP 06006961 dated Oct. 22, 2007.
European Search Report EP 06006963 dated Aug. 4, 2006.
Int'l Search Report EP 06008515.6 dated Jan. 8, 2009.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
Int'l Search Report EP 07 004429.2 dated Nov. 2, 2010.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
Int'l Search Report EP 07 014016 dated Jan. 28, 2008.
European Search Report EP 07015191.5 dated Jan. 23, 2008.
European Search Report EP 07015601.3 dated Jan. 4, 2008.
European Search Report EP 07015602.1 dated Dec. 20, 2007.
Int'l Search Report EP 07 016911 dated May 28, 2010.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
European Search Report EP 07253835.8 dated Dec. 20, 2007.
European Search Report EP 08001019 dated Sep. 23, 2008.
Int'l Search Report EP 08 002692.5 dated Dec. 12, 2008.
Int'l Search Report EP 08 004655.0 dated Jun. 24, 2008.
European Search Report EP 08004975 dated Jul. 24, 2008.
European Search Report EP 08006731.7 dated Jul. 29, 2008.
Int'l Search Report EP 08 006732.5 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
Int'l Search Report EP 08 006917.2 dated Jul. 3, 2008.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
Int'l Search Report EP 08 016539.2 dated Jan. 8, 2009.
European Search Report EP 08019920.1 dated Mar. 27, 2009.
European Search Report EP 08020530.5 dated May 27, 2009.
Int'l Search Report EP 08 020807.7 dated Apr. 24, 2009.
European Search Report EP 08169973.8 dated Apr. 6, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
European Search Report EP 09010873.9 extended dated Nov. 13, 2009.
European Search Report EP 09010877.0 extended dated Dec. 3, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
European Search Report EP 09151621 dated Jun. 18, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
European Search Report EP 09156861.8 dated Aug. 4, 2009.
Int'l Search Report EP 09 160476.9 dated Aug. 4, 2009.
European Search Report EP 09161502.1 dated Sep. 2, 2009.
European Search Report EP 09161502.1 extended dated Oct. 30, 2009.
Int'l Search Report EP 09 164903.8 dated Aug. 21, 2009.
Int'l Search Report EP 09 165753.6 dated Nov. 11, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
Int'l Search Report EP 09 168153.6 dated Jan. 14, 2010.
Int'l Search Report EP 09 168810.1 dated Feb. 2, 2010.
European Search Report EP 09169376.2 extended dated Dec. 16, 2009.
European Search Report EP 09172188.6 extended dated Apr. 23, 2010.
Int'l Search Report EP 09 172749.5 dated Dec. 4, 2009.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
Int'l Search Report EP 10 000259.1 dated Jun. 30, 2010.
European Search Report EP 10004950.1 extended dated Jul. 2, 2010.
European Search Report EP 10004951.9 extended dated Jul. 2, 2010.
Int'l Search Report EP 10 157500.9 dated Jul. 30, 2010.
European Search Report EP 10158944.8 extended dated Jun. 21, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
European Search Report EP 10161722.3 extended dated Jun. 16, 2010.
European Search Report EP 10163235.4 dated Aug. 10, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
International Search Report PCT/US98/18640 dated Jan. 29, 1999.
International Search Report PCT/US98/23950 dated Jan. 14, 1999.
Int'l Search Report PCT/US98/24281 dated Feb. 22, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.

International Search Report PCT/US03/37110 dated Jul. 25, 2005.
International Search Report PCT/US03/37111 dated Jul. 28, 2004.
International Search Report PCT/US03/37310 dated Aug. 13, 2004.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
Int'l Search Report PCT/US07/021438 dated Apr. 1, 2008.
Int'l Search Report PCT/US07/021440 dated Apr. 8, 2008.
International Search Report PCT/US08/052460 dated Apr. 24, 2008.
Int'l Search Report PCT/US08/61498 dated Sep. 22, 2008.
International Search Report PCT/US09/31658 dated Mar. 11, 2009.
Int'l Search Report PCT/US09/032690 dated Jun. 16, 2009.
International Search Report PCT/US10/032796 dated Jul. 28, 2010.

* cited by examiner

APPARATUS AND METHOD FOR ELECTRODE THERMOSURGERY

CROSS-REFERENCE TO RELATED APPLICATION

The present application is a continuation application of U.S. patent application Ser. No. 11/418,880 entitled "APPARATUS AND METHOD FOR ELECTRODE THERMOSURGERY" filed by Ronald J. Podhajsky on May 5, 2006, now U.S. Pat. No. 7,846,158, the entire contents of which are hereby incorporated by reference herein.

BACKGROUND

1. Technical Field

The present disclosure relates to an electrosurgical system and method. More particularly, the present disclosure relates to an apparatus and method for tissue ablation having increased electrode temperature control.

2. Background of Related Art

Therapeutic lesions in living bodies have been accomplished for many decades using radio-frequency (RF) and other forms of energy. The procedures have been particularly useful in the field of neurosurgery, typically where RF ablation electrodes (usually of elongated cylindrical geometry) are inserted into a living body. A typical form of such ablation electrodes incorporates an insulated sheath from which an exposed (uninsulated) tip extends.

Generally, the ablation electrode is coupled between a grounded RF power source (outside the body) and a reference ground or indifferent electrode for contacting a large surface of the body. When an RF voltage is provided between the reference electrode and the inserted ablation electrode, RF current flows from the ablation electrode through the body. Typically, the current density is very high near the tip of the ablation electrode, which heats and destroys the adjacent tissue.

Ablation electrode techniques, including the theory behind the techniques and many applications of the techniques are described in various papers, specifically see, (1) Cosman et al, "Theoretical Aspects of Radiofrequency Lesions in the Dorsal Root Entry Zone" Neurosurg 15:945-950, 1984 and (2) Cosman E. R. and Cosman B. J.: "Methods of Making Nervous System Lesions, in Wilkins R H, Rengachary S S (EDS): Neurosurgery, New York, McGraw-Hill, Vol. III, pp. 2490-2498, 1984.

In the past, RF ablation electrodes have incorporated temperature sensors, for example, in the form of a thermistor or thermocouple. In that regard, see U.S. Pat. No. 4,411,266 (1983, Eric R. Cosman). Typically, the sensor is connected to a monitoring apparatus for indicating temperature to assist in accomplishing a desired lesion. As generally known, for a given tip geometry and tip temperature, lesions of a prescribed size can be made quite consistently. In that regard also, see U.S. Pat. No. 4,411,266, (1983, Eric R. Cosman).

Over the years, a wide variety of RF electrode shapes and configurations have been used, for example, several current forms are available from ValleyLab Inc., Boulder, Colo. Such electrodes have been used to accomplish lesions in a wide variety of targets within the body, including the brain, the spinal column and the heart.

However, a limitation of prior electrode ablation systems relates to the temperature of the tip. Specifically, prior ablation electrodes of a given tip geometry should not effectively exceed a temperature of 100.degree. C. At that temperature, the surrounding tissue will boil and char. Also, uncontrolled disruption, such as hemorrhage and explosive gas formation, may cause extremely hazardous and clinically dangerous effects on the patient. Consequently, the lesion size for a given electrode geometry generally has been considered to be somewhat limited by the fact that the tissue near the tip must not exceed 100.degree. C.

Essentially, during RF ablation, the electrode temperature is highest near the tip, because the current density is the highest at that location. Accordingly, temperature falls off as a function of distance from the electrode tip, and except for possible abnormalities in tissue conductivity, in a somewhat predictable and even calculable pattern. As an attendant consequence, the size of RF lesions for a given electrode geometry have been somewhat limited.

One proposed solution to the limitation of lesion's size has been to employ "off-axis" electrodes, for example the so called Zervas Hypophysectomy Electrode or the Gildenberg Side-Outlet electrode, as manufactured by Integra Radionics, Inc, Burlington, Mass. However, such systems in requiring multiple tissue punctures, increase the risk of hemorrhage, severely prolong the time of surgery and increase the level of delicacy. An umbrella of off-axis lesions may not produce a desired homogenous or uniform lesion.

SUMMARY

Accordingly, the present disclosure is directed to an electrosurgical instrument for use with a source of electrical energy to ablate tissue in a living subject. In one embodiment, the instrument includes an elongated tissue-penetrating electrode including a rigid tubular member with a closed distal end defining an interior cavity extending from the closed distal end to a proximal end of the rigid tubular member. The rigid tubular member defines an electrically conductive surface capable of receiving electrical energy from a source of electrical energy. The instrument also includes at least one electrically conductive segment located on the elongated tissue-penetrating electrode. Each electrically conductive segment is configured to receive electrosurgical energy from the rigid tubular member. The instrument also includes an insulation layer, disposed upon the elongated tissue-penetrating electrode, that defines an exposed portion of the elongated tissue-penetrating electrode at the distal end. The instrument further includes at least one sensor that detects temperature during ablation. A semiconductive material coated on the rigid tubular member forms at least one resistive layer configured to connect the rigid tubular member with a corresponding electrically conductive segment.

Each resistive layer and the corresponding electrically conductive segment generate a thermal geometry related to the resistance of the resistive layer. The thermal geometries formed by each electrically conductive segment forms a thermal geometry related to the electrosurgical instrument. The resistive layer may be constructed from a material deposition process, a removal process, spin deposition, lithography, evaporators, ion beam etching and/or chemical etching.

The electrosurgical instrument may also include a control line which, when activated, allows electrical current to flow from the rigid tubular member. The activation of the control line allows electrical current to flow from the rigid tubular member, through each resistive layer and to the corresponding electrically conductive segment.

The electrosurgical instrument may further include a fluid conduit sized to extend into the interior cavity of the rigid tubular member. The fluid conduit is connected to a source of coolant and supplies coolant that cools tissue contiguous to the exposed portion of the elongated tissue-penetrating electrode. The source of coolant may be an adjustable source that adaptively provides coolant to the fluid conduit according to the detected temperature.

The present disclosure is also directed to a system for targeting and ablating a volume of tissue to maximize the formation of a lesion. The system includes an electrical energy generator and an elongated tissue-penetrating electrode. The elongated tissue-penetrating electrode includes one or more sensors that detect a temperature during ablation and a rigid tubular member having a closed distal end that defines an interior cavity. The interior cavity extends from the closed distal end to a proximal end. The rigid tubular member defines an electrically conductive surface capable of receiving electrical energy from the electrical energy generator. One or more electrically conductive segments are located on the elongated tissue-penetrating electrode and are configured to receive electrosurgical energy from the rigid tubular member. A semiconductive material, coated on the rigid tubular member, forms one or more resistive layers. The layers each configured to connect the rigid tubular member with a corresponding electrically conductive segment. An insulation layer, disposed on the elongated tissue-penetrating electrode, defines an exposed portion of the elongated tissue-penetrating electrode at the distal end. A fluid conduit, sized to extend into the interior cavity of the rigid tubular member, has a first end in fluid communication with an adjustable fluid source and a second end in fluid communication with the rigid tubular member. The adjustable fluid source adaptively provides coolant to the fluid conduit.

Each respective resistive layer and the corresponding electrically conductive segment generate a thermal geometry related to the resistance of the resistive layer. In one embodiment, the resistance of a first resistive layer is different than the resistance of a second resistive layer. The thermal geometries formed by each of the electrically conductive segments forms a thermal geometry related to the electrosurgical instrument.

The system may include a control line which, when activated, allows electrical current to flow from the rigid tubular member. Activation of the control line allows electrical current to flow from the rigid tubular member, through each resistive layer and to each corresponding electrically conductive segment.

The present disclosure is also directed to a method for targeting and ablating a volume of tissue to maximize the formation of a lesion. The method includes the steps of providing an elongated tissue-penetrating electrode including a rigid tubular member and having one or more electrically conductive segment disposed on the elongated tissue-penetrating electrode; coating a semiconductive material on the rigid tubular member, the semiconductive material forming one or more resistive layers configured to connect the rigid tubular member with a corresponding electrically conductive segments; detecting a temperature using at least one sensor during ablation; supplying electrical energy from a generator to the rigid tubular member; supplying coolant to the rigid tubular member according to the detected temperature using an adjustable source of coolant; controlling a flow of electrical energy from the rigid tubular member to the at least one electrically conductive segment; and controlling a flow of coolant from the adjustable source of coolant to the rigid tubular member.

The method may further include the steps of activating a control line which, when activated, allows electrical current to flow from the rigid tubular member. Another method may include the step of generating a thermal geometry related to the resistance of a resistive layer coated on the rigid tubular member.

BRIEF DESCRIPTION OF THE DRAWINGS

Various embodiments of the present disclosure are described herein with reference to the drawings wherein:

FIG. 4A is an enlarged block and sectional diagram of an alternate embodiment of the present disclosure showing a plurality of fixed resistors;

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems.

Figure 1:
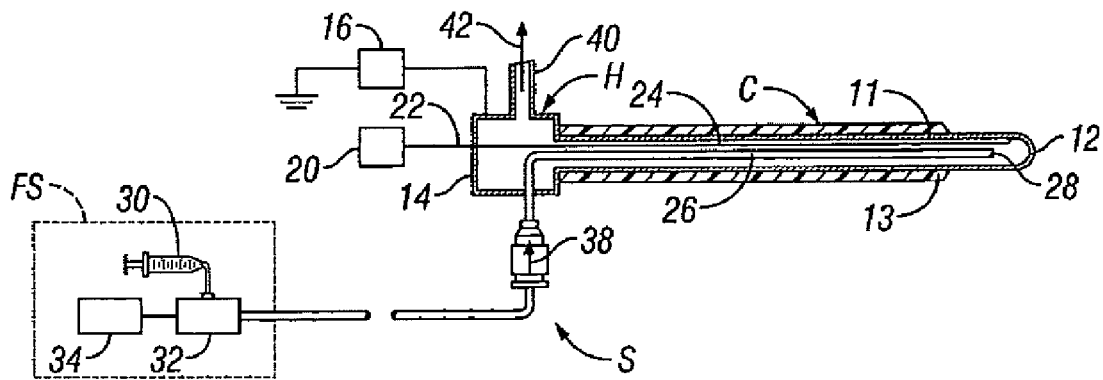
FIG. 1 is a block and sectional diagram of a system constructed in accordance with a prior art device.
Figure 2:
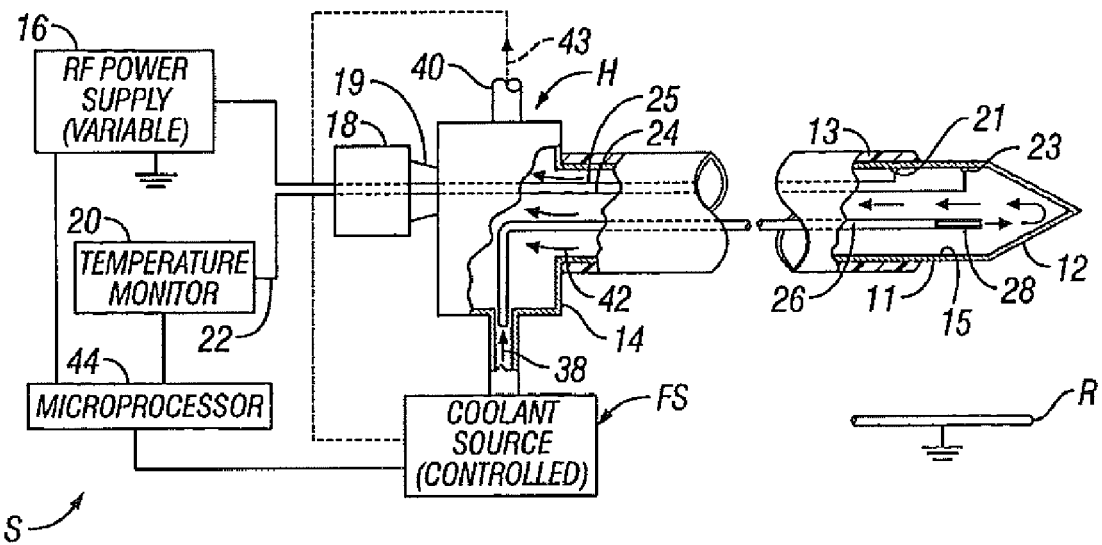
FIG. 2 is an enlarged block and sectional diagram of the prior art illustrating portions of the system of FIG. 1 in greater structural detail and with slight modifications.

Referring concurrently to FIGS. 1 and 2, the illustrated ablation system generally incorporates an elongated shaft or cannula body C for insertion, either percutaneously or intraoperatively into an open wound site. As illustrated, the cannula body C is integral with a head or hub element H coupled to remote support components, collectively designated S.

Structurally, cannula body C incorporates an elongated ablative electrode 11 (FIG. 2) formed of conductive material, e.g. metal such as stainless steel, titanium, etc. At the distal end of the cannula body C, electrode 11 defines a tip 12 that may be radiused at its end or which may be pointed. In one form, tip 12 may define a trocar point and may be of robust metal construction to facilitate insertion or penetration of tissue. In operation, when using an R.F. power supply 16, electrical current spreads from tip 12 to pass through the surrounding tissue causing the tissue to heat up. That is, when tip 12 is positioned contiguous (near, touching or within) to tissue, energy from R.F. power supply 16 is dissipated into heat within the tissue.

Over most of its length, electrode 11 carries an insulative coating 13 for selectively preventing the flow of electrical current from shaft 15 of electrode 11 into surrounding tissue. Thus, insulative coating 13 shields the intervening tissue from RF current, so that such tissue is not substantially heated along the length of shaft 15 except by the heating effect from exposed tip 12. Insulative material 13 may be constructed from a variety of different materials, including, but not limited to, ceramics, glass and polymeric materials.

The proximal end of electrode 11 (FIG. 2) is integral with an enlarged housing 14 of hub H that carries electrical and coolant connections, as explained in greater detail below.

Outside the patient's body, housing 14 may be of a cylindrical configuration, defining ports for connections to the support components S, i.e., electrical and fluid couplings. As suggested, housing 14 may be integral with electrode 11, formed of metal, or it may constitute a separate subassembly as described below. Alternatively, housing 14 can be of plastic, accommodating separate electrical connections. In that regard, a plastic housing 14 is amenable to low artifact imaging by X-rays, CT, MRI, etc. as may be desirable in some situations.

Housing 14 mates with a block 18 (FIG. 2) defining a luer taper lock 19, essentially sealing block 18 to housing 14. Thus, fluid and electrical couplings are provided. Specifically, connection to a regulated RF supply 16 (variable) can take the form of a standard cable connector, a leader wire, a jack-type contact or other designs known in the high frequency art. The temperature-sensing and radiofrequency electrical connections can be made through housing 14 and extend to the region of tip 12, where an RF line 25 is connected by junction 21 (a weld, braze, or other secure electrical connection). Sensor lines 24 extend to a thermo-sensor 23, as in the form of a thermistor, or a thermocouple, or other type of sensor. Thermo sensor 23 may be fused or in thermal contact with the wall of tip 12 to sense the temperature of tip 12.

RF power supply 16 may be referenced to reference potential as illustrated (FIG. 2), and coupled through block 18 affixed to hub H. Specifically, RF power supply 16 provides RF current through line 25, which extends through block 18 and on to connection junction 21 located on electrode 11. Power supply 16 may take the form of an RF generator as exemplified by the RFG-3C RF Lesion Generator System available from ValleyLab, Inc., Boulder, Co.

As indicated above and in accordance with common practice, when ablation electrode 11 is in a patient's body, an electrical circuit is completed through the body to a reference or dispersive electrode R (symbolically represented in FIG. 2) that is connected elsewhere to the body. Consequently RF power supply 16 heats body tissue by sending current from tip 12. In that regard, a temperature monitor 20 (FIG. 2 left, center) may be electrically connected by line 22 to temperature sensor 23 as in the form of a thermocouple or thermistor typically within or contacting tip 12. As illustrated, sensor 23 is connected to tip 12. The sensed temperature may be utilized to control either or both the flow of RF energy or the flow of coolant to attain the desired ablation. Note that a plurality of sensors could be utilized including those that could extend outside tip 12 to measure temperatures existing at various locations in the proximity of tip 12. Temperature monitor 20 may be as exemplified by the TC thermocouple temperature monitoring devices available from ValleyLab, Inc., Boulder, Colo.

In accordance herewith, temperatures at or near tip 12 (manifest by monitor 20) may be controlled by controlling the flow of fluid coolant through ablation electrode 11. Accordingly, the temperature of the tissue contacting or near tip 12 is controlled. In the disclosed embodiment, fluid from a fluid source FS is carried the length of ablation electrode 11 (FIG. 2) through a tube 26 extending from housing H to the distal end of electrode 11 terminating in an open end 28 at tip 12. At the opposite end of electrode 11, within housing H, tube 26 is connected to receive fluid. As illustrated in the detailed structure of FIG. 1, fluid source FS includes a source unit 34 coupled through a control 32 utilizing a hypodermic syringe 30 to actuate fluid flow (arrow 38) through a coupling 38. Thus, fluid flow is regulated in accordance with observed temperature, allowing increased flow of RF energy.

The fluid coolant may take the form of water or saline for the convection removal of heat from tip 12. Reservoir or source unit 34 (FIG. 1) might be a large reservoir of cooled water, saline or other fluid. As a simplistic example, a tank of water with ice cubes can function to maintain the coolant at a temperature of approximately 0° C. As another example, the fluid source FS could incorporate a peristaltic pump or other fluid pump, or could merely be a gravity feed for supplying fluid from a bag or rigid tank.

Flow away from tip 12 (FIG. 2) exits hub H through an exit port 40, as illustrated by arrows 42 and 43. Note that the ports may take the form of simple couplings, rigid units or may comprise flexible tubular couplings to reduce torque transmission to the electrode 11. Also, the coolant flow members may take the form of PVC tubes with plastic luer connectors.

As a result of the coolant flow, the interior of electrode 11, in particular electrode tip 12, can be held to a temperature near that of the fluid source FS. The coolant can circulate in a closed system as illustrated in FIG. 2. Also, in some situations, it may be desirable to reverse the direction of fluid flow from that depicted in the figures. As treated in detail below, coordinated operation involving RF heating along with the cooling may be accomplished by a microprocessor 44 (FIG. 2). In that regard, microprocessor 44 is coupled to RF power supply 16, temperature monitor 20 and fluid source FS to receive data on flow rates and temperatures and exercise control. Accordingly, an integrated operation is provided with feedback from temperature monitor 20 in a controlled format and various functions can be concurrently accomplished. Thus, facilitated by the cooling, the temperature profile of ablation electrode 11 may be moderated, changed, controlled or stabilized. Such controlled operation can effectively reduce the temperature of tissue near tip 12 to accomplish an equilibrium temperature distribution tailored to the desired lesion size.

The temperature distribution in the tissue near tip 12 depends on the RF current from tip 12 and depends on the temperature of the tissue that is adjacent to tip 12 and that tip temperature can be controlled to approach the temperature of the fluid from the source FS. Thus, a thermal boundary condition may be established, holding the temperature of the tissue (near tip 12) to approximately the temperature of the tip itself, e.g. the temperature of the fluid inside tip 12. Accordingly, by temperature control, a surgeon may impose a defined temperature at the boundary of electrode tip 12, which can be somewhat independent of the RF heating process and, in fact, dramatically modify the temperature distribution in the tissue.

Heat is generated in the following manner during ablation. The area of the ablation electrode 11 that is in contact with the ablation site (i.e., the tip 12) affects the current density of the signal that heats the tissue. The smaller the contact area the ablation electrode 11 has with the tissue, the greater the current density and the greater and more concentrated the heating of tissue. Conversely, the greater the contact area of the ablation electrode 11, the smaller the current density and the less heating of tissue. Further, the greater the heating of tissue, the greater the probability of burning the tissue. It is therefore important to either ensure a relative high amount of contact area between the ablation electrode 11 and the tissue, or otherwise maintain a relatively low current density on the ablation electrode 11.

While there are various methods of maintaining a relatively low current density (including the use of electrosurgical return electrode monitors (REMs), such as the one described in commonly-owned U.S. Pat. No. 6,565,559, the entire contents of which are incorporated by reference herein), the present disclosure ensures ablation electrode 11 maintains a low current density by controlling the temperature created by the current over the surface of the ablation electrode 11.

Figure 3A:
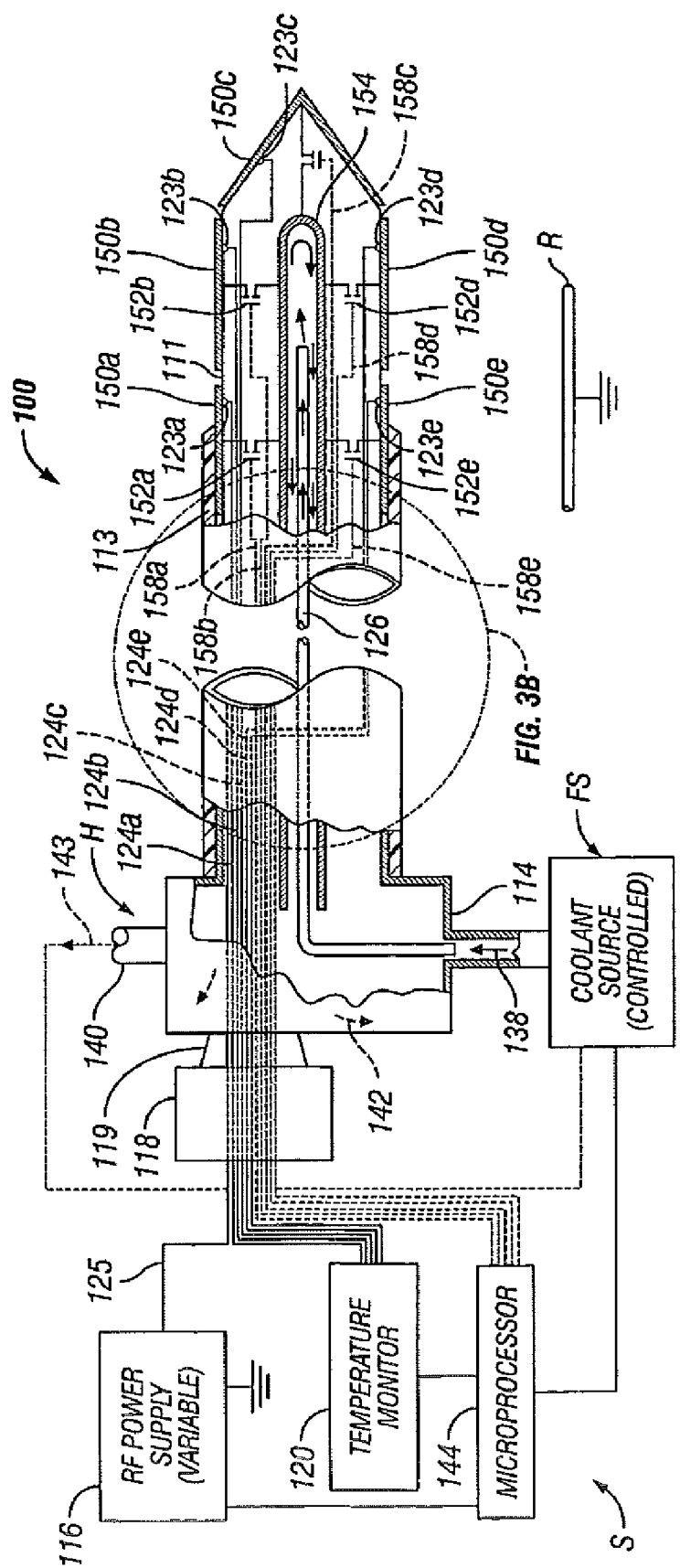
FIG. 3A is a greatly enlarged block and sectional diagram of the present disclosure showing a plurality of electrically conductive segments.
Figure 3B:
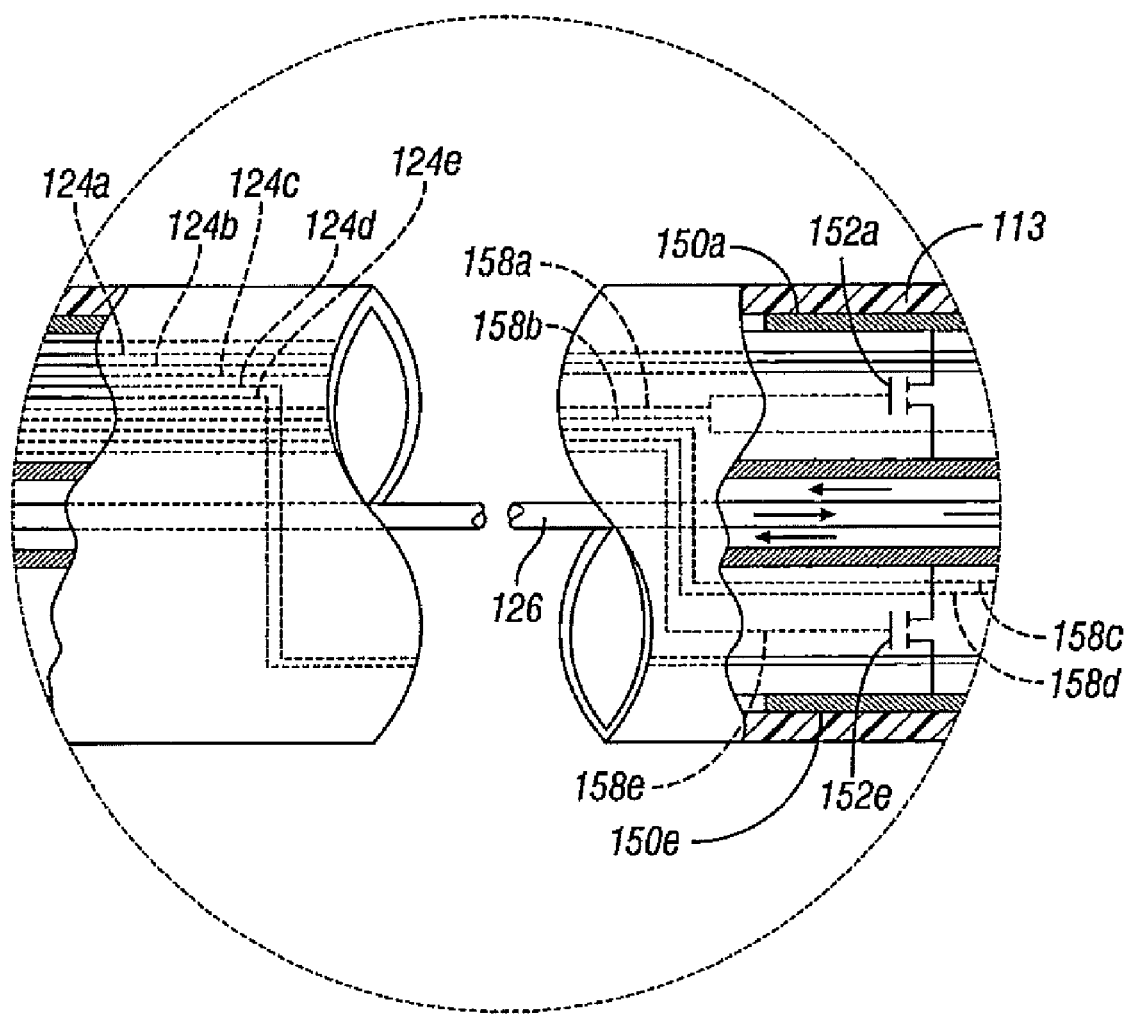
FIG. 3B is a view of the area of detail in FIG. 3A.

Referring now to FIGS. 3A and 3B, one embodiment of electrosurgical instrument 100 according to the present disclosure is shown for use with a source of electrical energy to ablate tissue in a living subject. Electrosurgical instrument 100 includes electrode 111 having a rigid tubular member 154 contained therein. Rigid tubular member 154 is electrically conductive and is operatively connected to RF power supply 116 as discussed in greater detail below. Electrically conductive segments 150a-e are disposed on the exterior surface of electrode 111. Segments 150a-e are configured to receive electrosurgical energy from the rigid tubular member 154 as also discussed in greater detail below. Electrode 111 also includes an insulation layer 113 disposed upon segments 150a-e and/or electrode 111. Insulation layer 113 defines an exposed portion of instrument 100, and may be constructed from a variety of suitable materials, such as those mentioned above.

Electrically conductive segments 150a-e are each connected to rigid tubular member 154 by respective transistors 152a-e. The gate of each transistor 152a-e is connected to a respective control line 158a-e, which leads to a microprocessor 144 or control unit that controls the flow of electrical energy to segments 150a-e. In this arrangement, transistors 152a-e act as switches that provide control over the energy output profile delivered to respective segments 150a-e. Activation of any particular control line triggers current flow from rigid tubular member 154 to the selected segment 150 (e.g., activation of control line 158b allows current to flow from rigid tubular member 154, through transistor 152b to segment 152b). Microprocessor 144 may be housed within and may work in conjunction with an electrosurgical generator (not explicitly shown) to regulate and control the various transistors.

Rigid tubular member 154 may be coated with a suitable semiconductive material in order to create transistors 152a-e. Transistors 152a-e may be constructed from a variety of different designs, including, but not limited to, Metal Oxide Semiconductor Field Effect Transistors (MOSFETs). These may be created using techniques known in the semiconductor industry, such as those used in the construction of integrated circuits. For a more detailed explanation of MOSFETs and their construction see CMOS VLSI DESIGN: A CIRCUITS AND SYSTEMS PERSPECTIVE, by N. Weste et al., Pearson Education, Boston, Mass., 2005.

Rigid tubular member 154 includes a closed distal end and defines an interior cavity extending from the closed distal end to a proximal end of rigid tubular member 154. Tubular member 154 contains a fluid conduit or tube 126. Tube 126 is sized to extend into the interior cavity and is adapted to be connected to a source of coolant "FS" to supply coolant for cooling tissue. Coolant source "FS" may be an adjustable source of coolant for adaptively providing coolant to fluid conduit 126 according to the detected temperature. As mentioned above, coolant source "FS" may work in conjunction with microprocessor 144, RF power supply 116 and temperature monitor 120 to adjust coolant flow in order to achieve the desired temperature.

In FIG. 3, temperature sensors 123a-e and corresponding temperature lines 124a-e are similar to those described herein above and shown in FIG. 2 as temperature sensor 23 and corresponding temperature line 24. However, sensors 123a-e provide the temperature status of respective segments 150a-e, therefore allowing for a more detailed temperature profile. Temperature lines 124a-e may be connected to temperature monitor 120, microprocessor 144 or both. Using the data obtained from temperature sensors 123a-e the levels of RF current and coolant may be adjusted to achieve the desired results and to optimize instrument performance.

Figure 4B:
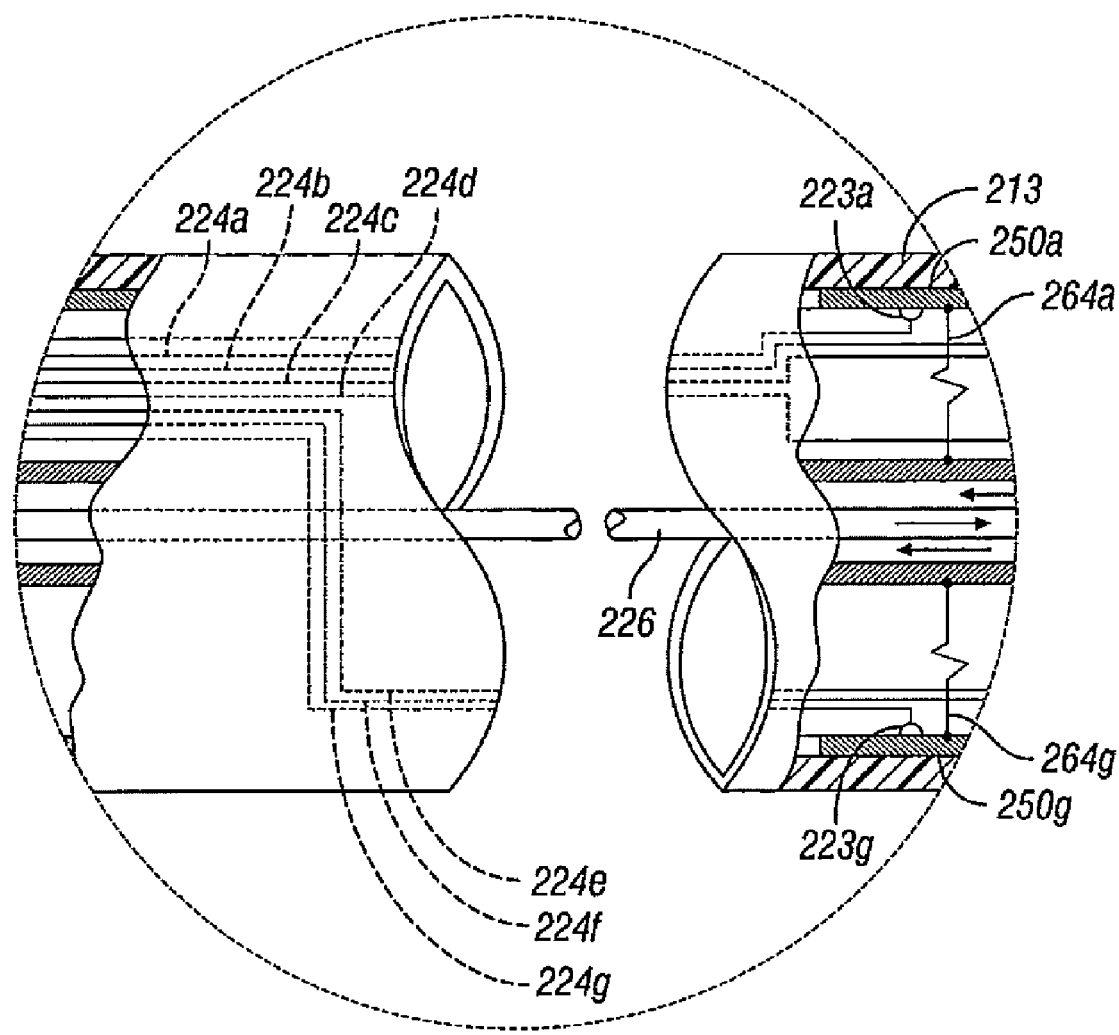
FIG. 4B is a view of the area of detail of FIG. 4A.

Referring now to FIGS. 4A-4B, an alternate embodiment of an electrosurgical instrument 200 according to the present disclosure is shown. FIG. 4 is similar to FIG. 3 above but replaces transistors 152 and corresponding control lines 156 with resistive layers 264a-g having a known fixed resistance. The fixed resistance values are selected so that a desired thermal profile is continuously provided. Using this configuration, instruments having numerous thermal geometries may be manufactured. Some of these thermal geometries may include, but are not limited to, spherical, cylindrical, conical, nonsymmetrical, polygonal etc.

Construction of fixed resistive layers is common in silicon wafer fabrication and similar techniques may be utilized here. Resistors are often built into integrated circuits as part of the fabrication process, using a semiconductor as the resistor. Electrode fabrication may utilize, inter alia, the following processes and devices: material deposition or removal processes, spin deposition, lithography, evaporators, ion beam etching and silicon beam etching.

RF power supply 216, temperature monitor 220, microprocessor 244 and coolant source "FS" all work in conjunction to produce a desired ablative effect. Instrument 200 works in a similar fashion to that described above in FIGS. 3A-38 but includes fixed resistors 264.

Figure 5:
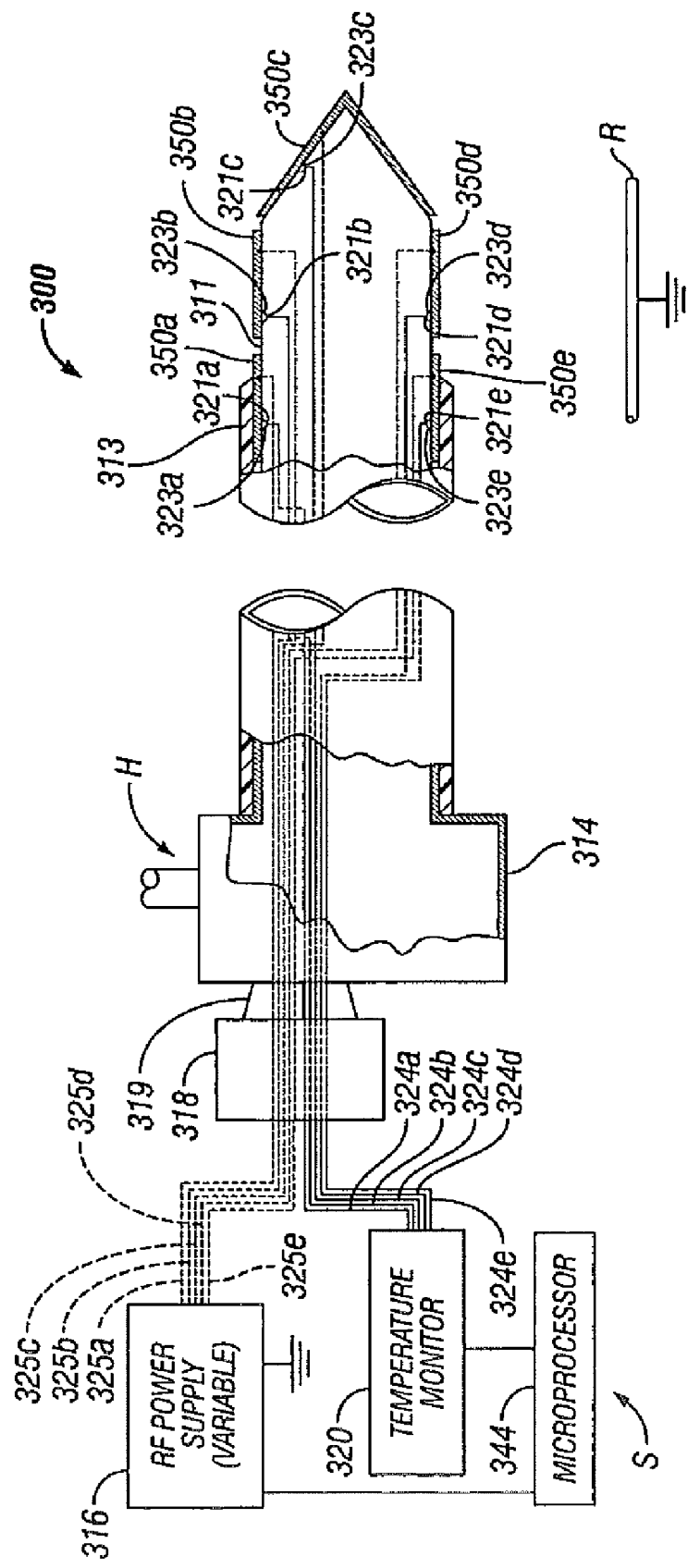
FIG. 5 is an enlarged block and sectional diagram of another embodiment of the present disclosure showing a plurality of electrically conductive segments having a direct connection with an electrical energy source.

FIG. 5 shows another embodiment of electrosurgical instrument 300 according to the present disclosure which includes rigid tubular member 154 of previous embodiments. In this embodiment, direct RF connections are made between RF Power Supply 316 and individual segments 350a-e. The amount of RF energy delivered to each segment 350a-e can be controlled using the microprocessor (which may be part of an electrosurgical generator (not shown)) to provide improved shaping of the thermal profile. Certain elements may utilize either monopolar or bipolar energy.

The present disclosure also relates to a method for targeting and ablating a volume of tissue to maximize the formation of a lesion. The method includes the step of providing an elongated tissue-penetrating electrode 111 including a rigid tubular member 154 with a closed distal end defining an interior cavity extending from the closed distal end to a proximal end of rigid tubular member 154. Rigid tubular member 154 defines an electrically conductive surface capable of receiving electrical energy from the source of electrical energy (such as an electrosurgical generator). The method also includes the step of placing at least one electrically conductive segment 150 on electrode 111. Segment 150 may be configured to receive electrosurgical energy from rigid tubular member 154. The method also includes the step of disposing an insulation layer 113 upon the elongated tissue-penetrating electrode 111, thereby defining an exposed portion of electrode 111 at the distal end. The method may also include the step of detecting the temperature of each electrically conductive segment 150 using a sensor 123 disposed upon each segment 150.

The method may further include the steps of supplying electrical energy (such as RF) from a generator or energy source to rigid tubular member 154 and supplying coolant through fluid conduit 126 to the closed distal end of rigid tubular member 154. The coolant flow may be selectively adjustable depending upon the measured temperature. The method may further include the step of controlling the flow of electrical energy from rigid tubular member 154 to each segment 150 using one or more microprocessors 144. Similarly, the method provides the step of controlling a flow of coolant from an adjustable source of coolant to the distal end of the rigid tubular member using one or more microprocessors 144. In certain embodiments, the step of activating a control line in order to allow electrical current to flow from rigid tubular member 154 to electrically conductive segment 154 may be included.

From the above description, it will be apparent to persons skilled in the art that the present invention may be embodied in a number of various forms. In that regard, the embodiment shown in the figures may be implemented variously, for example, to be either disposable or non-disposable. The thermal circulation system may or may not be an intact closed end, tissue-penetrating structure. Temperature sensors and monitors may or may not be used in the electrode or applicator.

Various forms of plastics, metals and composite materials may be utilized to accomplish specific objectives. For example, insulation coating 13 may take the form of Teflon, polyethylene, and the like. Numerous alternative embodiments of the present disclosure are envisioned.

Various energy sources could be employed as alternatives to RF energy. As examples, the energy could take the form of microwave energy, an ultrasonic heater providing sonic waves into tissue or a direct power source. Also as indicated, heating could be directed by various shapes of structures or variously apertured structures.

Alternative electrodes may take the form of a cannula with fiber optic channels to transmit laser light into the tissue for the generation of heat at a depth. Various geometries (curved or straight) of laser systems may be employed as well. One form of RF power supply may comprise the RFG-3C Lesion Generator as produced by ValleyLab, Inc., Boulder, Colo., however, other suitable electrical power sources such as electrosurgical RF power supplies, bipolar cautery supplies, etc. could be utilized as well.

Various graphics displays may be incorporated in accordance herewith along with the cooling system as disclosed. Various controls may be provided for the cooling system and the heating system coordinated by observed or displayed phenomena. Various forms of feedback control are well-known and may be utilized in the present disclosure. For a detailed description of modern feedback control systems see FEEDBACK CONTROL OF DYNAMIC SYSTEMS, by G. Franklin et al., Prentice-Hall, Upper Saddle River, N.J., 2002.

As explained with respect to the disclosed embodiments, many variations of electrodes or body terminals are practical including tubular shafts, square shafts, etc. Flat electrodes, area electrodes, multiple electrodes, arrays of electrodes, electrodes with side-outlet or side-issued-tips, electrodes with balloon tips, expandable tips or conformable tips can be considered within the system. Electrodes with steerable tips and electrode shafts that can be conformed or shaped or that can be malleable can be considered within the system. Electrodes that are designed to be placed within the body tissue or on the surface of the body or within cavities within the bodies can be devised, which are encompassed herewith. Electrodes may or may not have temperature sensors within them or near them and, for instance, the ablation process can be done by supplying heating power and applicator cooling without temperature monitoring or control but merely using empirical parameters, such as heating power and cooling fluid temperature/flow.

While several embodiments of the disclosure are shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument for use with a source of electrical energy to ablate tissue in a living subject, the instrument comprising:
    an elongated tissue-penetrating electrode including a rigid tubular member having a closed distal end defining an interior cavity extending from the closed distal end to a proximal end of the rigid tubular member, the rigid tubular member defining an electrically conductive surface capable of receiving electrical energy from a source of electrical energy;
    at least one electrically conductive segment located on the elongated tissue-penetrating electrode, the at least one electrically conductive segment configured to receive electrosurgical energy from the rigid tubular member;
    an insulation layer disposed on the elongated tissue-penetrating electrode defining an exposed portion of the elongated tissue-penetrating electrode at the distal end;
    at least one sensor that detects temperature of tissue during ablation; and
    a semiconductive material directly coated on the rigid tubular member and forming at least one resistive layer configured to connect the rigid tubular member with a corresponding at least one electrically conductive segment.

2. The electrosurgical instrument according to claim 1, wherein the at least one resistive layer generates a thermal geometry related to the resistance of the at least one resistive layer.

3. The electrosurgical instrument according to claim 1, further comprising a control line which, when activated, allows electrical current to flow from the rigid tubular member.

4. The electrosurgical instrument according to claim 3, wherein activation of the control line allows electrical current to flow from the rigid tubular member, through each of the at least one resistive layer and to the corresponding at least one electrically conductive segment.

5. The electrosurgical instrument according to claim 2, wherein the thermal geometry formed by each of the at least one electrically conductive segment is related to the electrosurgical instrument.

6. The electrosurgical instrument according to claim 5, wherein the at least one resistive layer is constructed from a process selected from the group consisting of a material deposition process, a removal process, spin deposition, lithography, evaporators, ion beam etching and chemical etching.

7. The electrosurgical instrument according to claim 1, further comprising a fluid conduit sized to extend into the interior cavity of the rigid tubular member and adapted to be connected to a source of coolant to supply coolant that cools tissue contiguous to the exposed portion of the elongated tissue-penetrating electrode.

8. The electrosurgical instrument according to claim 7, wherein a source of coolant is an adjustable source of coolant that adaptively provides coolant to the fluid conduit according to a detected temperature.

9. A system for targeting and ablating a volume of tissue to maximize the formation of a lesion, the system comprising:
    an electrical energy generator;
    an elongated tissue-penetrating electrode including a rigid tubular member having a closed distal end defining an interior cavity extending from the closed distal end to a proximal end of the rigid tubular member, the rigid tubular member defining an electrically conductive surface capable of receiving electrical energy from the electrical energy generator;

at least one electrically conductive segment located on the elongated tissue-penetrating electrode, the at least one electrically conductive segment configured to receive electrosurgical energy from the rigid tubular member;

a semiconductive material directly coated on the rigid tubular member and forming at least one resistive layer configured to connect the rigid tubular member with a corresponding at least one electrically conductive segment;

an insulation layer disposed on the elongated tissue-penetrating electrode defining an exposed portion of the elongated tissue-penetrating electrode at the distal end;

at least one sensor that detects a temperature during ablation; and a fluid conduit sized to extend into the interior cavity of the rigid tubular member, the fluid conduit having a first end in fluid communication with an adjustable fluid source, and a second end in fluid communication with the rigid tubular member, wherein the adjustable fluid source adaptively provides coolant to the fluid conduit.

10. The system according to claim 9, wherein the at least one resistive layer generates a thermal geometry related to the resistance of the at least one resistive layer.

11. The system according to claim 9, further comprising a control line which, when activated, allows electrical current to flow from the rigid tubular member.

12. The system according to claim 11, wherein activation of the control line allows electrical current to flow from the rigid tubular member, through the at least one resistive layer and to the corresponding at least one electrically conductive segment.

13. The system according to claim 9, wherein the at least one resistive layer includes a first resistive layer and a second resistive layer and the resistance of the first resistive layer is different than the resistance of the second resistive layer.

14. The system according to claim 13, wherein the first resistive layer generates a first thermal geometry, the second resistive layer generates a second thermal geometry and the first and second resistive layers generate an elongated tissue-penetrating electrode thermal geometry.

15. A method for targeting and ablating a volume of tissue to maximize the formation of a lesion, the method comprising:

providing an elongated tissue-penetrating electrode including a rigid tubular member and having at least one electrically conductive segment disposed on the elongated tissue-penetrating electrode;

directly coating a semiconductive material on the rigid tubular member, the semiconductive material forming at least one resistive layer, the at least one resistive layer configured to connect the rigid tubular member with the at least one electrically conductive segment;

detecting a temperature using at least one sensor during ablation;

supplying electrical energy from a generator to the rigid tubular member;

supplying coolant to the rigid tubular member according to the detected temperature using an adjustable source of coolant;

controlling a flow of electrical energy from the rigid tubular member to the at least one electrically conductive segment; and controlling a flow of coolant from the adjustable source of coolant to the rigid tubular member.

16. The method according to claim 15, further comprising the step of activating a control line configured to allow the electrical energy to flow from the rigid tubular member.

17. The method according to claim 15, further comprising the step of generating a thermal geometry related to the resistance of the at least one resistive layer directly coated on the rigid tubular member.

\* \* \* \* \*